United States Patent [19]

Hozumi et al.

[11] Patent Number: 4,551,532

[45] Date of Patent: Nov. 5, 1985

[54] ETHYLENE GLYCOL DERIVATIVES HAVING ANTI-PROTOZOAN, ANTI-FUNGAL AND ANTI-TUMOR ACTIVITY

[75] Inventors: Motoo Hozumi, Omiya; Hiroaki Nomura, Takatsuki; Yoshio Yoshioka, Kitakatsurag, all of Japan

[73] Assignee: Takeda Chemical Industries, Ltd., Osaka, Japan

[21] Appl. No.: 257,771

[22] Filed: Apr. 27, 1981

[30] Foreign Application Priority Data

May 8, 1980 [JP] Japan .................... 55-61463
Feb. 20, 1981 [JP] Japan .................... 56-24460

[51] Int. Cl.[4] .................. C07F 9/40; C07F 9/58; C07F 9/60; C07F 9/65
[52] U.S. Cl. .................. 546/22; 546/23; 548/112; 544/178; 544/232; 544/337; 260/945; 514/77
[58] Field of Search ............. 546/22, 23; 548/112; 544/178, 232, 337; 260/945

[56] References Cited

U.S. PATENT DOCUMENTS 3,708,558 1/1973 Kny et al. .................... 260/945

FOREIGN PATENT DOCUMENTS 2642661 3/1978 Fed. Rep. of Germany ...... 260/945
772649 2/1978 South Africa ................ 260/945

*Primary Examiner*—Alan L. Rotman
*Attorney, Agent, or Firm*—Wegner & Bretschneider

[57] ABSTRACT

New ethylene glycol derivatives, inclusive of salts thereof, which have the formula:

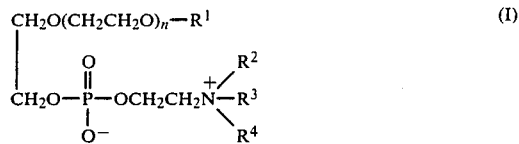

wherein n is an integer of 1 to 15; $R^1$ is an aliphatic hydrocarbon group containing 6 to 26 carbon atoms; $R^2$, $R^3$ and $R^4$ are independently H or lower alkyl, or

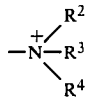

represents a cyclic ammonio group, exhibit inhibitory activity to multiplication of tumor cells and antimicrobial activity.

12 Claims, No Drawings

ETHYLENE GLYCOL DERIVATIVES HAVING ANTI-PROTOZOAN, ANTI-FUNGAL AND ANTI-TUMOR ACTIVITY

This invention relates to novel ethylene glycol derivatives which are of value as medicines or antifungal agents.

More particularly, this invention relates to ethylene glycol derivatives, inclusive of salts thereof, which have the formula:

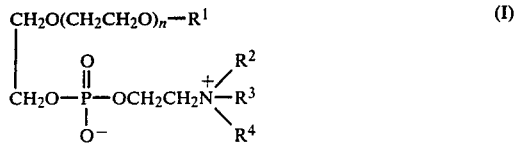

wherein n is an integer of 1 to 15; $R^1$ is an aliphatic hydrocarbon group containing 6 to 26 carbon atoms; $R^2$, $R^3$ and $R^4$ are independently H or lower alkyl, or

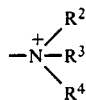

represents a cyclic ammonio group.

Referring to the above formula (I), $R^1$ for an aliphatic hydrocarbon residue of 6 to 26 carbon atoms which may be straight-chain or branched, saturated or unsaturated includes, for example, $C_{6-26}$ alkyls, $C_{6-26}$ alkenyls and $C_{6-26}$ alkynyls, preferably $C_{8-26}$ alkyls and $C_{8-26}$ alkenyls, and these groups may be further substituted by OH, mercapto, amino, oxo, carbamoyl, carboxyl, halogen, $C_{3-7}$ cycloalkyl, phenyl, etc. Specific examples of $R^1$ are $C_{10-20}$ alkyl [e.g. n-dodecyl, n-tridecyl, n-tetradecyl, n-pentadecyl, n-heptadecyl, n-eicosanyl, n-docosanyl, dihydrophytyl], $C_{10-20}$ alkenyl [e.g. 8-tridecenyl($\Delta^8$), 8-tetradecenyl($\Delta^8$), 8,11-tetradecadienyl($\Delta^{8,11}$), heptadecenyl($\Delta^8$), 1-heptadecenyl($\Delta^1$), 8,11,14-heptadecatrienyl($\Delta^{8,11,14}$), 8,11-octadecadienyl($\Delta^{8,11}$), 4,7,10,13-nonadecateraenyl($\Delta^{4,7,10,13}$), phytyl, 12-(2,3-cyclopentenyl)dodecyl, 12-(2,3-cyclopentenyl)-5-dodecenyl, 11-hydroxy-8-heptadecenyl, 3,7-dimethyl-9-(2,6,6-trimethyl-1-cyclohexen-1-yl)-2,4,6,8-nonatetraenyl], $C_{14-24}$ aralkyl [e.g. 15-(4-n-butylphenoxy)pentadecyl, ω-(p-tolyl)heptadecyl, 6-(4-pentylphenoxy)hexadecyl, 4,7,10,13-nondecatetraynyl, heptadeca-8-ynyl, etc.]

Referring to $R^2$, $R^3$ and $R^4$ which represent H or lower alkyl, the lower alkyl is exemplified by $C_{1-5}$ alkyl (e.g. methyl, ethyl, n-, iso- or tert-butyl). When at least one or more of $R^2$, $R^3$ and $R^4$ are H (e.g. $R^2$=H), the compound (I) can be represented by the formula:

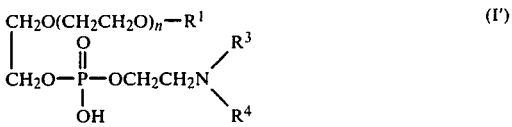

wherein the symbols have the same meanings as defined hereinbefore.

The cyclic amino group

includes, for example, pyridinio, oxazolio, thiazolio, pyridazinio, quinolinio, isoquinolinio, etc., each of which may have such substituent groups as $C_{1-4}$ alkyl (e.g. methyl, ethyl), hydroxyl, hydroxyethyl, aminoethyl, amino (imino), carbamoyl, ureido, etc. Further species of said cyclic ammonio group includes cases in which any two members of $R^2$, $R^3$ and $R^4$ form a ring structure with the quaternary nitrogen atom, with the remaining one member being a $C_{1-4}$ alkyl groups (e.g. methyl, ethyl). Thus, for example, N-methylmorpholino, N-methylpiperadinio, etc. may be further mentioned.

In the present compounds, a preferred embodiment is a compound (I) wherein n is an integer of 1 to 15; $R^1$ is $C_{6-26}$ alkyl, $C_{6-26}$ alkenyl or $C_{6-26}$ alkynyl, each of said groups being unsubstituted or substituted by hydroxyl, mercapto, amino, oxo, carbamoyl, carboxyl, halogen, $C_{3-7}$ cycloalkyl or phenyl; and $R^2$, $R^3$ and $R^4$ are independently hydrogen or $C_{1-5}$ alkyl, or

represents cyclic ammonio selected from the group consisting of pyridinio, oxazolio, thiazolio, pyridazinio, quinolinio, isoquinolinio, N-$C_{1-4}$ alkylmorpholinio and N-$C_{1-4}$ alkylpiperazino, each of said groups being unsubstituted or substituted by $C_{1-4}$ alkyl, hydroxyl, hydroxyethyl, aminoethyl, amino, carbamoyl or ureido, or a pharmaceutically acceptable salt thereof.

Referring further, to formula (I), n is an integer of 1 to 15, preferably 1 to 9, especially 1 to 4.

It should be understood that the compound (I) may also exist in the form of a salt having the formula:

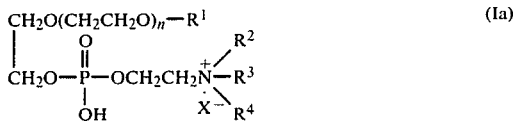

wherein n and $R^1$ are defined above, and $X^-$ is an anion (e.g. $Cl^-$, $Br^-$, or $I^-$), or a salt of the formula:

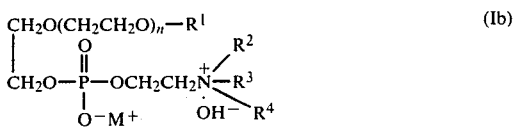

wherein n and $R^1$ are as defined above, and $M^+$ is an alkali metal (e.g. Na, K) ion or an alkaline earth metal (e.g. Ca, Mg) ion.

The Compound (I) of this invention can be produced by, for example, the following methods.

METHOD A

A compound of the formula:

$$\text{CH}_2\text{O}(\text{CH}_2\text{CH}_2\text{O})_n-\text{R}^1 \quad \text{(II)}$$
$$|$$
$$\text{CH}_2\text{OH}$$

[wherein n and $R^1$ are as defined hereinbefore] is reacted with a compound of the formula:

$$\begin{array}{c} X \\ \diagdown \\ X \end{array} \!\! P\!\!-\!\!\text{OCH}_2\text{CH}_2.Y \quad \text{(III)}$$

[wherein X and Y each is halogen (e.g. Cl, Br, I)] to give a compound of the formula:

$$\text{CH}_2\text{O}(\text{CH}_2\text{CH}_2\text{O})_n-\text{R}^1 \quad \text{(IV)}$$
$$|\qquad\quad\;\; \text{O}$$
$$\quad\qquad\quad\;\;\; \|$$
$$\text{CH}_2\text{O}-\text{P}-\text{OCH}_2\text{CH}_2-Y$$
$$|$$
$$X$$

[wherein $R^1$, n, X and Y each is as defined hereinbefore] and, then, water is permitted to act on the last-mentioned compound (IV) to give a compound of the formula:

$$\text{CH}_2\text{O}(\text{CH}_2\text{CH}_2\text{O})_n-\text{R}^1 \quad \text{(V)}$$
$$|\qquad\quad\;\; \text{O}$$
$$\quad\qquad\quad\;\;\; \|$$
$$\text{CH}_2\text{O}-\text{P}-\text{OCH}_2\text{CH}-Y$$
$$|$$
$$\text{OH}$$

[wherein $R^1$, n and Y are respectively defined hereinbefore]

This compound (V) is further reacted with a compound of the formula:

$$\begin{array}{c} R^2 \\ \diagup \\ N-R^3 \\ \diagdown \\ R^4 \end{array} \quad \text{(VI)}$$

[wherein the symbols have the meanings respectively defined hereinbefore] to give the desired compound (I).

The compound (II) used in the above method can be prepared by the known method, e.g. the method described in Oda R. and Teramura K.: The Synthesis and Application of Surfactants (Kaimenkassei-zai-no-gosei-to-sono-ohyo), Maki Shoten, pp. 141–143.

When at least 2 members of $R^2$, $R^3$ and $R^4$ are H, the following method B can be utilized.

METHOD B

The compound (II) is reacted with a compound of the formula:

$$\begin{array}{c} X \\ \diagdown \\ X \end{array} \!\! P\!\!-\!\!\text{OCH}_2\text{CH}_2\text{N} \!\!\begin{array}{c} \diagup R' \\ \diagdown R'' \end{array} \quad \text{(III')}$$

[wherein X is as defined hereinbefore; either R' or R" is $R^2$ and another is a protective group (e.g.,. —COOCH$_2$C$_6$H$_5$, —COOC$_6$H$_5$, —CHO, —COCF$_3$, —COCH$_2$C$_6$H$_5$ or —SiMe$_3$, —C(C$_6$H$_5$)$_3$), or R' and R", on cyclization with the adjacent N atom, represent $$-\text{N}\!\!\begin{pmatrix} \text{succinimide} \end{pmatrix} \text{ or } -\text{N}\!\!\begin{pmatrix} \text{phthalimide} \end{pmatrix},$$

followed by treatment with water and removal of the protective group an adequate method known per se, to give a compound which belongs to the compound (I) and is represented by the formula:

$$\text{CH}_2\text{O}(\text{CH}_2\text{CH}_2\text{O})_n-\text{R}^1 \quad \text{(I'')}$$
$$|\qquad\quad\;\; \text{O}$$
$$\quad\qquad\quad\;\;\; \|$$
$$\text{CH}_2\text{O}-\text{P}-\text{OCH}_2\text{CH}_2\overset{+}{\text{N}}\text{H}_2\text{R}^2$$
$$|$$
$$\text{O}^-$$

[wherein $R^1$, $R^2$ and n are as defined hereinbefore].

METHOD C

A compound of formula (II) is reacted with a phosphorylating agent to give a compound of the formula:

$$\text{CH}_2\text{O}(\text{CH}_2\text{CH}_2\text{O})_n-\text{R}^1 \quad \text{(VII)}$$
$$|\qquad\quad\;\; \text{O}\;\; X$$
$$\quad\qquad\quad\;\;\; \|\diagup$$
$$\text{CH}_2\text{OP}$$
$$\diagdown$$
$$X$$

[wherein $R^1$, n and X are as defined hereinbefore], which is then reacted with a compound of the formula:

$$\text{HOCH}_2\text{CH}_2\text{N}\!\!\begin{array}{c} \diagup R' \\ \diagdown R'' \end{array} \quad \text{(VIII)}$$

[wherein R' and R" are as defined hereinbefore], followed by treatment with water and removal of the protective group to give a compound (I''), or a compound (VII) is reacted with a compound of the formula:

$$\text{HOCH}_2\text{CH}_2\text{Z} \quad \text{(IX)}$$

[wherein Z is $$-\overset{+}{\text{N}}\!\!\begin{array}{c} \diagup R^2 \\ -R^3 \\ \diagdown R^4 \end{array}$$

or Y as defined hereinbefore], to give the compound (I) or compound (V). The compound (V) can be converted to the compound (I) by the method previously mentioned.

The compound (I) of this invention and salts thereof have growth inhibiting and cell differentiation (decarcinogenesis) inducing activities against tumor cells (e.g. mouse spontaneous leukemia cells MI, Rauscher virus-induced mouse leukemia cells R-453, human myelocytic leukemia cells HL60). It also has an antitumor activity in in vivo tumor systems where the rate of tumor growth is relatively slow.

On that occasion, not only cytocidal and differentiation inducing activities but also immunopotentiation activities are observed. More specifically, they show a life span prolonging action when administered to tumor-bearing animals such as mice or rats with spontaneous tumor, carcinogen-induced solid tumor or Ehrlich carcinoma, or nude mice transplanted with human tumor cells.

The compounds of this invention are of relatively low toxicity. For example, the compound of Example 7 causes no deaths in $CDF_1$ mice even at an intraperitoneal dose of 100 mg/kg (observation period: one week). The hemolytic activity of these compounds is also low in general. For example, in a hemolysis test (with human erythrocytes) by the method of Gottfried et al. [J. Lipid Research, 4, 57 (1963)], the 50% hemolytic concentration of the compound of Example 15 was about 10 μg/ml. In the presence of 5% human albumin, the concentration was several times as high (the hemolytic activity being several times as low).

The present compound can be administered as an antitumor agent to a warm-blooded animal afflicted by malignant tumors such as leukemia, and can produce significant life-span prolonging effect. Generally, the compound of the present invention represented by formula (I) is obtained in the form of a crystalline powder or a powder, and is sufficiently hydrophilic as well as lipophilic. When the compound is used as an antitumor agent, it can safely be administered parenterally or orally as a variety of pharmaceutical composition such as injectable solution, tablet, capsule, solution or ointment.

Injectable solutions, solutions for drip infusion and the like containing the compound can be prepared in a conventional manner using, for example, physiological saline or an aqueous solution containing glucose and/or other auxiliaries. Tablets, capsules and the like can also be prepared in a conventional manner. These are prepared as unit dosage forms and applied by an adequate route of administration depending on the purpose of administration thereof. In the case of injectable solutions, for instance, they are administered by intravenous or subcutaneous injection or directly applied to the affected resion. The dose for tumor-bearing warm-blooded animals can adequately be determined depending on the symptom, route of administration, etc., generally within the range of about 0.05–75 mg/kg body weight, preferably within the range of about 0.5–30 mg/kg body weight. As to the frequency of dosing, the drug can be administered daily or at 2- to 5-day intervals. It is also possible to administer the drug 1–4 times a day or by intravenous drip infusion so as to maintain the drug concentration in tissues at a required level for a prolonged period of time.

Furthermore, the compound (I) of this invention has antifungal or antimycotic activity. Such antimycotic activity includes, among others, the activity against Trichophyton, *Cryptococcus neoformans* and yeasts. Therefore, the compound (I) is useful in the treatment and prevention of diseases caused by these fungi, such as trichophytia. Antimycotic preparations containing the Compound (I) can be produced in a conventional manner. The amount of the active ingredient is not critical, but, when the preparations are used in the treatment of trichophytia, for instance, the amount of the compound of this invention is generally about 0.01–70% by weight, preferably about 0.1–5% by weight, based on the whole preparation. The antimycotic preparations can be administered in a conventional manner. Thus, for example, they are advantageously applied to or sprayed on the affected part once to several times a day.

The compound (I) of this invention is also active against phytopathogenic pests, especially fungi, hence is also useful as an agricultural fungicide for combating such plant diseases as rice blast, rice Helminthosporium leaf spot, rice stem rot, gray mold and cucumber anthracnose. Agricultural fungicide preparations containing the compound are made in a conventional manner. Adequate contents of the active ingredient are generally about 10–90% for emulsifiable concentrates, wettable powders and the like, about 0.1–10% for solutions, dusts and the like, and about 5–50% for granular preparations. Emulsifiable concentrates, wettable powders and the like should preferably be sprayed after adequate dilution with water or the like (e.g. 50–5,000-fold dilution). The agricultural fungicide preparations are applied by various methods known per se in such a manner that the active ingredient be applied generally in an amount of about 10–300 g per 10 ares and the concentration of the active ingredient desirably be in the range of about 10–1,000 ppm.

The compound (I) of this invention is only sparingly active against bacteria in general and yet is active against protozoa (e.g. Tetrahymena), which activity in association with the aforesaid antimycotic activity thereof makes the compound (I) of value as an antimycotic/antiprotozoal agent for the assay of bacterial ecologies in the soil, activated sludge, body fluids, etc. Thus, for example, in isolating useful bacteria from the soil, or in detecting the activity of bacteria alone to the exclusion of protozoa and fungi for operation or analysis of the activated sludge process in waste water treatment, selective growth of bacteria is possible without allowing fungi and protozoa present in the sample to grow. More detailedly, the test sample is added to a liquid or solid culture medium, then 0.1 ml of an aqueous solution of the compound (I) having a concentration of about 10 μg/ml to 100 mg/ml is added, and incubation is performed.

The following examples and test examples illustrate the present invention in more detail. However, they are by no means limitative of the present invention.

EXAMPLE 1

3,6,9,12,15-Pentaoxaheptacosyl 2-bromoethyl phosphate

A mixture of 10.2 g (25.1 millimoles) of 3,6,9,12,15-pentaoxaheptacosyl alcohol and 6.68 g (27.6 millimoles) of 2-bromoethyl phosphorodichloridate in carbon tetrachloride is refluxed for 3 hours and then concentrated in dryness under reduced pressure. To the residue is added 30 ml of water, and the mixture is heated for 3 hours. The reaction mixture is extracted with 30 ml of chloroform, the extract concentrated to dryness, the residue dissolved in toluene and column-chromatographed on silica gel with toluene—$CHCl_3$ and MeOH—$CHCl_3$ being used in this order as eluents, and fractions containing the desired product are combined and concentrated to dryness to give 10.0 g of the title compound as an oily substance.

TLC[$SiO_2$, $CHCl_3$, MeOH:$H_2O$ (65:25:4)] Rf=0.55, one spot.

EXAMPLE 2

3,6,9,12,15-Pentaoxaheptacosyl 2-pyridinioethyl phosphate

In 15 ml of pyridine is dissolved 3.3 g (5.56 millimoles) of the bromide obtained in Exmaple 1, and the solution is stirred overnight at room temperature, followed by concentration to dryness. The residue is dissolved in 20 ml of methanol, 3.0 g of $Ag_2CO_3$ added, the mixture stirred under reflux for 30 minutes, the hot mixture filtered to remove the insoluble matter, the mother liquor concentrated to dryness under reduced pressure, the residue dissolved in a $CHCl_3$—MeOH—$H_2O$ mixture and column-chromatographed on silica gel using the same mixture as eluent, and fractions containing the desired product are combined, concentrated to dryness under reduced pressure, followed by thorough drying and purification with $CHCl_3$—acetone, to give 2.0 g of the title compound as a colorless oil substance.

Infrared absorption spectrum [IR] (film): 3420, 2930, 2855, 1630, 1490, 1460, 1350, 1220, 1070, 940.

Elemental analysis: Calculated for $C_{29}H_{54}O_9NP \cdot H_2O$: C, 57.12; H, 9.26; N, 2.30; P, 5.08. Found: C, 57.00; H, 9.43; N, 2.20; P, 5.15.

EXAMPLE 3

3,6,9,12,15-Pentaoxaheptacosyl 2-trimethylammonioethyl phosphate

In 25 ml of 20% trimethylamine-toluene is dissolved 2.4 g (4.04 millimoles) of the bromide obtained in Example 1, and the solution is heated in a sealed tube at 60° C. The reaction mixture is concentrated to dryness under reduced pressure, the residue dissolved in methanol, 2.5 g of $Ag_2CO_3$ added, the mixture stirred under reflux, the insolubles removed by filtration when hot, and the mother liquor concentrated to dryness under reduced pressure. The residue is dissolved in a $CHCl_3$—MeOH—$H_2O$ mixture and column-chromatographed on silica gel using the same mixture as eluent, and fractions containing the desired product are combined and concentrated to dryness under reduced pressure, followed by purification with $CHCl_3$—acetone, to give 1.25 g of the title compound as an oil.

IR (film): 3400, 2925, 2855, 1630, 1465, 1350, 1290, 1220, 1085, 960, 765.

Elemental analysis: Calculated for $C_{27}H_{58}NO_9P \cdot 2H_2O$: C, 53.36; H, 10.28; N, 2.30; P, 5.10. Found: C, 53.20; H, 10.28; N, 2.35; P. 5.40.

EXAMPLE 4

3,6-Dioxatetracos-15(Z)-en-1-ol

To a mixture of 11.2 g of KOH (powder), 16.96 g 160 millimoles) of diethylene glycol and 100 ml of DMSO is added 14.35 g (50 millimoles) of oleyl chloride, and the mixture is stirred for 4 hours. The reaction mixture is poured into water, and neutralized with conc-HCl. The resulting precipitate is collected by filtration, and dissolved in a mixture of 200 ml of $CHCl_3$ and 200 ml of $H_2O$. After separation from the aqueous layer, the $CHCl_3$ layer is concentrated to dryness under reduced pressure. The residue is column-chromatographed on silica gel using 2% MeOH—$CHCl_3$ (v/v) as eluent. Fractions containing the desired product are collected and concentrated to dryness under reduced pressure.

There is obtained 12 g of the title compound as a colorless oil.

IR (film): 3450, 3000, 2920, 2850, 1460, 1115, 1060.
NMR (60MC, $d_6$-DMSO): 1.8–2.33 (31H), 3.17–3.83(10H), 4.50(1H), 5.37(2H).

EXAMPLE 5

3,6-Dioxatetracos-15(Z)-enyl 2-aminoethyl phosphate 2.0 g (5.6 millimoles) of the alcohol obtained in Example 4 and 2.24 g (7.27 millimoles) of 2-phthalimidoethyl phosphorodichloridate are dissolved in benzene, then 0.88 g (11.2 millimoles) of pyridine is added dropwise, and the mixture is stirred at room temperature. The reaction mixture is concentrated to dryness under reduced pressure, the residue dissolved in a pyridine-water mixture, and the solution stirred at 70° C. and then poured into a diluted HCl. After ether extraction, the extract is concentrated to dryness under reduced pressure. The residue is dissolved in MeOH containing 1.25 g of hydrazine hydrate, and the solution refluxed. After cooling, $CHCl_3$ is added to the reaction mixture, the insoluble matter filtered off, and the filtrate concentrated to dryness under reduced pressure. The residue is dissolved in a $CHCl_3$—MeOH—$H_2O$ mixture and column-chromatographed on silica gel using the same mixture as eluent. Fractions containing the desired product are combined and concentrated to dryness under reduced pressure, and the residue is recrystallized from acetone—$CHCl_3$ to give 1.6 g of the title compound as a colorless crystalline powder.

IR (film): 3410, 3000, 2920, 2850, 1630, 1550, 1460, 1220, 1140, 1080, 1000, 950, 920, 790, 760.

Elemental analysis: Calculated for $C_{24}H_{50}NO_6P \cdot 0.5H_2O$: C, 58.99; H, 10.52; N, 2.87; P, 6.33. Found: C, 59.28; H, 10.35; N, 3.02; P, 6.27.

EXAMPLE 6

3,6-Dioxatetracos-15(Z)-enyl 2-bromoethyl phosphate

In carbon tetrachloride is dissolved in 3.57 g (10 millimoles) of the alcohol obtained in Example 4, then 2.9 g (12 millimoles) of 2-bromoethyl phosphorodichloridate is added, and 1.19 g (15 millimoles) of pyridine is added dropwise. The mixture is stirred at room temperature, and then concentrated to dryness under reduced pressure. Water is added, the mixture heated, then acidified with hydrochloric acid, and extracted with ether. The ether layer is washed with water, and concentrated to dryness under reduced pressure to give 3.5 g of the desired product as a solid.

EXAMPLE 7

3,6-Dioxatetracos-15(Z)-enyl 2-trimethylammonioethyl phosphate

In 10 ml of trimethylamine-toluene is dissolved 1.08 g (2 millimoles) of the bromide obtained in Example 6, and the solution is heated in a sealed tube at 60° C. The reaction mixture is treated by the procedure of Example 2 including dehalogenation with $Ag_2CO_3$. Isolation of the desired product by silica gel chromatography gives 9.8 g of the title compound as a colorless solid.

IR (film): 3400, 2930, 2855, 1455, 1230, 1085, 1055, 970.

Elemental analysis: Calculated for $C_{27}H_{56}NO_6P \cdot 2H_2O$: C, 58.14; H, 10.84; N, 2.51; P, 5.55. Found: C, 58.10; H, 11.13; N, 2.48; P, 5.67.

EXAMPLE 8

3,6-Dioxatetracos-15(Z)-enyl 2-tert-butylaminoethyl phosphate

In 5 ml of toluene containing 5.0 g of tert-butylamine is dissolved in 1.08 g (2 millimoles) of the bromide obtained in Example 6, and the solution is stirred at room temperature. The reaction mixture is concentrated to dryness under reduced pressure, and the resiue is washed with acetone. The pale brown powder thus obtained is dissolved in chloroform, the insoluble matter filtered off, the filtrate concentrated, and acetone is added gradually to the concentrate. The resulting precipitate, when collected, gives 0.7 g of the title compound as a colorless powder.

IR (KBr): 2400, 2920, 2850, 2730, 2640, 2545, 1630, 1560, 1460, 1375, 1310, 1230, 1170, 1055, 980.

Elemental analysis: Calculated for $C_{28}H_{58}NO_6P \cdot H_2O$: C, 62.54; H, 11.25; N, 2.61; P, 5.76. Found: C, 62.57; H, 11.70; N, 2.41; P, 5.81.

EXAMPLE 9

3,6,9,12-Tetraoxatriacont-12(Z)-en-1-ol

To a solution of 1.08 g of NaH in tetrahydrofuran is added 31.04 g (160 millimoles) of tetraethylene glycol and further added 11.48 g (40 millimoles) of oleyl chloride, and the mixture is refluxed. The reaction mixture is poured into water, and extracted with ethyl acetate. The extract is concentrated to dryness under reduced pressure, and the residue is column-chromatographed on silica gel using MeOH—CHCl$_3$ as eluent. Fractions containing the desired product are combined and concentrated to dryness under reduced pressure to give 7.5 g of the title compound as a colorless solid.

TLC [silica gel, CHCl$_3$—MeOH (19:1)] Rf=0.61, one spot.

NMR (60MC, d$_6$-DMSO): 1.8–2.33(31H), 3.17–3.83(18H), 5.40(2H), 4.50(1H).

EXAMPLE 10

3,6,9,12-Tetraoxatriacont-21(Z)-enyl 2-aminoethyl phosphate

In benzene are dissolved 2.22 g (4.99 millimoles) of the alcohol obtained in Example 9 and 2.00 g (6.49 millimoles) of 2-phthalimidoethyl phosphorodichloridate, then 790 mg (10 millimoles) of pyridine is added dropwise, and the mixture is stirred at room temperature. The reaction mixture is treated by the procedure of Example 5 to give 1.38 g of the title compound as a colorless crystalline powder.

IR (film): 3400, 3000, 2920, 2850, 1630, 1550, 1460, 1210, 1150(sh.), 1070, 1000, 960, 915, 790.

Elemental analysis: Calculated for $C_{28}H_{58}NO_8P \cdot 0.5 H_2O$: C, 58.31; H, 10.31; N, 2.42; P, 5.37. Found: C, 58.52; H, 10.41; N, 2.42; P, 5.50.

EXAMPLE 11

3,6,9,12,15,18,21,24,27,30-Decaoxaoctatetracont-39(Z)-enyl 2-trimethylammonioethyl phosphate In carbon tetrachloride is dissolved in 7.09 g (10 millimoles) of 3,6,9.12,15,18,21,24,27,30-Decaoxaoctatetracont-39(Z)-enyl alcohol, then 10.0 g (41 millimoles) of 2-bromoethyl phosphodichloridate is added dropwise. The mixture is stirred at room temperature and then refluxed. The reaction mixture is evaporated to dryness under reduced pressure, water added to the residue and the mixture heated. After cooling, the mixture is extracted in sequence with ether and chloroform. The chloroform extract is evaporated to dryness under reduced pressure. The residue is dissolved in trimethylamine-toluene, and the solution is heated in a sealed tube at 60° C. The reaction mixture is treated by the procedure of Example 2. After dehalogenation with Ag$_2$CO$_3$ and the subsequent silica gel column chromatography, there is obtained 7.5 g of the title compound as a colorless solid.

TLC[SiO$_2$, CHCl$_3$—MeOH—H$_2$O (65:25:4)] R$_f$=0.21, one spot.

NMR (60MC, CDCl$_3$): 0.8–2.4(31H), 3.0–4.8(55H), 5.4(2H).

IR (film): 3400, 2930, 2860, 1650, 1465, 1350, 1240, 1100, 960.

Elemental analysis: Calculated for $C_{43}H_{88}NO_{14}P \cdot 3H_2O$: C, 55.64; H, 10.21; N, 1.51; P, 3.34. Found: C, 55.53; H, 10.03; N, 1.52; P, 3.51

EXAMPLE 12

2-[2-(Dodecyloxy)ethoxy]ethyl 2-aminoethyl phosphate

A solution of 2.74 g of 2-[2-(dodecyloxy)ethoxy]ethanol and 3.10 g of 2-phthalimidoethyl phosphorodichloridate in benzene is refluxed, and the solvent is then distilled off, followed by adding water and pyridine. The mixture is heated on a water bath at 70° C. After cooling, the reaction mixture is poured into diluted hydrochloric acid, followed by ether extraction. The ether layer is dehydrated and concentrated, a methanol solution containing 1 g of hydrazine hydrate is added to the residue, the resulting mixture is refluxed, and the methanol is then distilled off. Chloroform is added to the residue, the mixture warmed, and the insoluble matter removed by filtration. After concentration, the product is isolated by silica gel chromatography [the developing solvent being chloroform-methanol-water (65:25:4)] and recrystallized from methanol, giving 1.96 g of the desired product.

IR $\nu_{max}^{KBr}$(cm$^{-1}$): 2910, 1638, 1560, 1250, 1223, 1080.

NMR (90 MHz, D$_2$O) δ: 1.01(3H, brs), 1.42(20 H, brs), 3.2–4.5(14H, m)

Elemental analysis: Calculated for $C_{18}H_{40}NO_6P$: C, 54.39; H, 10.14; N, 3.52; P, 7.79. Found: C, 54.65; H, 9.95; N, 3.64; P, 7.90.

EXAMPLE 13

3,6,9-Trioxaheneicosanyl 2-aminoethyl phosphate

By a similar procedure to that of Example 12, 3.18 g of 3,6,9-trioxaheneicosan-1-ol and 3.10 g of 2-phthalimidoethyl phosphorodichloridate are reacted to give the title compound. Yield 1.69 g.

IR $\nu_{max}^{KBr}$(cm$^{-1}$): 2920(CH), 1641(OH), 1560, 1256, 1230(P=O), 1096.

Elemental analysis: Calculated for $C_{20}H_{44}NO_7P$: C, 54.40; H, 10.04; N, 3.17. Found: C, 54.55; H, 9.99; N, 3.18.

EXAMPLE 14

3,6,9,12-Tetraoxatetracosyanyl 2-aminoethyl phosphate

Starting with 2.52 g of 3,6,9,12-tetraoxatetracosanol and 2.2 g of 2-phthalimidoethyl phosphorodichloridate, the title compound is produced by a similar procedure to that of Example 12. Yield 1.80 g.

IR $\nu_{max}^{KBr}$(cm$^{-1}$): 2920(CH), 1640(OH), 1498, 1225(P=O), 1080(P—O, C—O—C).

NMR(60 MHz, D$_2$O): 0.94(3H, brs), 1.33(20H, brs), 3.2–4.6(22H).

Elemental analysis: Calculated for C$_{22}$H$_{48}$NO$_8$P·0.25-H$_2$O: C, 53.91; H, 9.97; N, 2.86. Found: C, 53.80; H, 9.67; N, 2.92.

EXAMPLE 15

2-[2-Dodecyloxy)ethoxy]ethyl 2-pyridinioethyl phosphate

A mixture of 6.2 of 2-[2-(dodecyloxy)ethoxy]ethanol and 5.5 g of 2-bromoethyl phosphorodichloridate in benzene is refluxed. The solvent is then distilled off, water is added to the residue, and the mixture is further refluxed. Ether extraction, dehydration and concentration give 2-[2-(dodecyloxy)ethoxy]ethyl 2-bromoethyl phosphate. The one-third amount of the thus-obtained bromide is dissolved in pyridine, and the solution heated at 60° C. The solvent is then distilled off, Ag$_2$CO$_3$ and methanol are added to the residue, followed by refluxing. The insolubles are filtered off, the filtrate concentrated, and the residue purified by silica gel chromatography to give the desired product.

IR $\nu_{max}^{KBr}$(cm$^{-1}$): 2920(CH), 1640(OH), 1560, 1250, 1250(P=O), 1070(P—O, C—O—C).

NMR (60 MHz, CDCl$_3$) δ: 0.90(3H, brs), 1.26(20H, brs), 3.2–4.7(12H), 5.10(2H, CH$_2$N$^+$), 8.0–8.8 & 9.48 (5H, pyridinio).

EXAMPLE 16

3,6,9-Trioxaheneicosanyl 2-pyridinioethyl phosphate

Starting with 2-bromoethyl phosphorodichloridate and 3,6,9-trioxaheneicosan-1-ol and following the procedure of Example 15, the title compound is prepared.

IR $\nu_{max}^{KBr}$(cm$^{-1}$): 2925(CH), 1640(OH), 1495, 1245(P=O), 1075(P—O, C—O—C).

EXAMPLE 17

3,6-Dioxatetracosyl alcohol 16.7 g (50 mM) of octadecyl bromide and 31.8 g of diethylene glycol are dissolved in 50 ml of dimethyl sulfoxide, then 11.2 g (200 mM) of powdery KOH is added, and the mixture is stirred at room temperature for 2 hours. The reaction mixture is poured into water and neutralized. The crystalline precipitate is collected by filtration, methanol is added, the insolubles are filtered off, and the filtrate is subjected to silica gel column chromatography for isolation/purification to give the desired compound as colorless needles. Yield 8.5 g.

EXAMPLE 18

3,6-Dioxatetracoxyl 2-trimethylammonioethyl phosphate 5.37 g (15 mM) of the monool obtained in Example 17 and 4.72 g (19.5 mM) of 2-bromoethyl phosphorodichloridate are dissolved in benzene, 1.54 g of pyridine is added, and the mixture is stirred at room temperature.

Thereafter, the reaction mixture is treated in the same manner as in Examples 6 and 7 to give the desired compound in the form of crystalline powder. Yield 3.8 g.

TLC [silica gel, CHCl$_3$—MeOH—H$_2$O (65:25:4), R$_f$=0.2]

IR (film) cm$^{-1}$: 3400, 2920, 2950, 1640, 1460, 1240, 1130, 1080, 1060, 960, 910, 750.

Elemental analysis: Calculated for C$_{27}$H$_{58}$NO$_6$P·2.5-H$_2$O: C, 57.01; H, 11.17; N, 2.46; P, 5.45. Found: C, 56.71; H, 10.91; N, 2.69; P, 5.96.

EXAMPLE 19

3,6-Dioxatetracosyl 2-aminoethyl phosphate 1.8 g (5.72 mM) of the monool obtained in Example 17 and 2.24 g (7.27 mM) of 2-phthalimidoethyl phosphorodichloridate are dissolved in a mixture of benzene and pyridine, and the solution is stirred at room temperature. The reaction mixture is treated in the same manner as in Example 5 to give 1.7 g of a colorless powder.

IR (KBr)cm$^{-1}$: 3400, 2900, 2850, 1630, 1550, 1460, 1250, 1220, 1150, 1075, 1010, 910, 830, 750.

Elemental analysis: Calculated for C$_{11}$H$_{48}$NO$_5$P·0.3-H$_2$O: C, 59.64; H, 11.06; N, 3.16; P, 6.99. Found: C, 59.66; H, 10.97; N, 3.36; P, 7.19.

TLC [silica gel, CHCl$_3$—MeOH—H$_2$O (65:25:4) R$_f$=0.40, one spot.]

EXAMPLE 20

3,6-Dioxadodecyl 2-trimethylammonioethyl phosphate 4.76 g (25 mM) of 3,6-dioxadodecyl alcohol prepared in the same manner as in Example 17 is dissolved in a benzene solution containing 9.075 g (37.5 mM) of 2-bromoethyl phosphorodichloridate, then 2.96 g (37.5 mM) of pyridine is added, and the mixture is stirred at room temperature. The mixture is subjected to hydrolysis, quaternization and dehalogenation in the same manner as in Example 18 to give 2.0 g of the desired product as an oil.

IR (film)cm$^{-1}$: 3450, 2925, 2850, 1650, 1480, 1220, 1080, 1050, 960, 790.

Elemental analysis: Calculated for C$_{15}$H$_{34}$NO$_6$P·2-H$_2$O: C, 46.03; H, 9.78; N, 3.58; P, 7.91. Found: C, 46.21; H, 10.10; N, 3.57; P, 8.11.

EXAMPLE 21

3,6-Dioxahexadecyl 2-trimethylammonioethyl phosphate 3.0 g (12.2 mM) of 3,6-dioxahexadecyl alcohol and 4.43 g (18.3 mM) of 2-bromoethyl phosphorodichloridate are dissolved in benzene, 1.45 g (18.3 mM) of pyridine is added, and the mixture is stirred at room temperature. The reaction mixture is treated in the same manner as in Example 18 to give 1.5 g of a colorless solid.

IR (film)cm$^{-1}$: 3400, 2930, 2855, 1650, 1480, 1235, 1210, 1130(sh), 1085, 1060, 960, 760.

Elemental analysis: Calculated for C$_{19}$H$_{42}$NO$_6$P·H$_2$O: C, 53.13; H, 10.33; N, 3.26; P, 7.21. Found: C, 53.16; H, 10.26; N, 3.33; P, 7.51.

EXAMPLE 22

3,6-Dioxahexadecyl 2-aminoethyl phosphate 3.0 g (12.2 mM) of 3,6-dioxahexadecyl alcohol and 4.88 g (15.86 mM) of 2-phthalimidoethyl phosphorodichloridate are dissolved in benzene, and 1.25 g (15.86 mM) of pyridine is added dropwise. The reaction mixture is treated in the same manner as in Example 5 to give 1.2 g of a colorless crystalline powder.

IR (film)cm$^{-1}$: 3450, 2920, 2850, 1650, 1550, 1460, 1220, 1140, 1080, 1000, 910, 830, 796, 760.

Elemental analysis: Calculated for C$_{16}$H$_{36}$NO$_6$P: C, 52.02; H, 9.82; N, 3.79; P, 8.36. Found: C, 51.97; H, 9.84; N, 3.86; P, 8.37.

EXAMPLE 23

2-[2-(Tetradecyloxy)ethoxy]ethanol

Using 13.9 g of tetradecyl bromide and 15.9 g of diethylene glycol and proceeding as in Example 17, there is obtained the title compound. Yield 6.1 g.

IR (film)cm$^{-1}$: 3425, 2920, 2850, 1470, 1120.

EXAMPLE 24

3,6-Dioxaeicosyl 2-aminoethyl phosphate

Using 3.03 g of 2-[2-(tetradecyloxy)ethoxy]ethanol and 3.70 g of 2-phthalimidoethyl phosphorodichloridate, and proceeding as in Example 5, there is obtained the title compound, which, on recrystallization from methanol, weighs 1.4 g.

IR $\nu_{max}^{KBr}$(cm$^{-1}$): 2920, 2845(CH), 1640, 1555, 1472(CH), 1252, 1230(P=O), 1080, 1001, 915, 835.

Elemental analysis: Calculated for $C_{20}H_{44}NO_6P$: C, 56.45; H, 10.42; N, 3.29; P, 7.28. Found: C, 56.61; H, 10.13; N, 3.57; P, 7.39.

EXAMPLE 25

3,6-Dioxaoctadecyl 2-trimethylammonioethyl phosphate

The bromide (4.6 g) obtained in Example 15 is dissolved in a solution of trimethylamine in toluene, and the mixture is allowed to stand at room temperature for 2 days. The solvent is then distilled off, and the residue is subjected to similar after-treatments, followed by purification by silica gel chromatography, to give 1.7 g of the title compound.

IR $\nu_{max}^{KBr}$(cm$^{-1}$): 3400(OH), 2920(CH), 1480, 1240(P=O), 1090(C—O—C), 970.

Elemental analysis: Calculated for $C_{21}H_{46}NO_6P \cdot 1.5-H_2O$: C, 54.06; H, 10.59; N, 3.00; P, 6.63. Found: C, 53.76; H, 10.44; N, 3.08; P, 6.75.

EXAMPLE 26

3,6-Dioxaeicosyl 2-trimethylammonioethyl phosphate

Reacting 3.0 g of 2-[2-(tetradecyloxy)ethoxy]ethanol with 2.9 g of 2-bromoethyl phosphorodichloridate and thereafter proceeding as in Example 11, there is obtained 2.1 g of the title compound.

IR $\nu_{max}^{KBr}$(cm$^{-1}$): 3350(OH), 2910(CH), 1470, 1230(P=O), 1070(C—O—C), 960.

Elemental analysis: Calculated for $C_{23}H_{50}NO_6P \cdot H_2O$: C, 56.88; H, 10.99; N, 2.88; P, 6.37. Found: C, 56.88; H, 11.34; N, 3.17; P, 6.33.

EXAMPLE 27

2-[2-(Tridecyloxy)ethoxy]ethanol 31.8 g (0.3 mole) of diethylene glycol and 27 g (0.1 mole) of 1-bromotridecane are dissolved in a mixture of DMSO and DMF, then 22.5 g (0.4 mole) of powdery KOH is added, and the mixture is stirred vigorously with heating under reflux. After cooling, the reaction mixture is poured into water, adjusted to pH 7.0 with concentrated hydrochloric acid, and extracted with ethyl acetate. The ethyl acetate extract is subjected to silica gel column chromatography using n-hexane-chloroform as eluent. The thus isolated and purified product weighs 16.2 g (yield 56%).

TLC [silica gel, CHCl$_3$:MeOH (25:4)] R$_f$=0.35, one spot.

IR (film)cm$^{-1}$: 3450, 2920, 2850, 1460, 1110, 750.

EXAMPLE 28

3,6-Dioxanonadecyl 2-pyridinioethyl phosphate 5 g (0.0173 mole) of 2-[2-(tridecyloxy)ethoxy]ethanol is dissolved in benzene, and 6.7 g (0.0277 mole) of 2-bromoethyl phosphorodichloridate and 2.19 g (0.0277 mole) of pyridine are added. After the reaction, the reaction mixture is subjected to hydrolysis with water under heating, then concentrated hydrochloric acid is added, and the mixture is extracted with ether. The ether layer is concentrated to dryness, the residue is dissolved in pyridine, and the mixture is allowed to stand at room temperature for 2 days and then purified in the same manner as in Example 15 to give 2.9 g (yield 35%) of a colorless powder.

IR (KBr)cm$^{-1}$: 3420, 2925, 2850, 1490, 1460, 1240, 1070.

TLC [silica gel, CHCl$_3$:MeOH:H$_2$O (65:25:4)]; R$_f$=0.25, one spot.

Elemental analysis: Calculated for $C_{24}H_{44}NO_6P \cdot 1.5-H_2O$: C, 57.58; H, 9.46; N, 2.80; P, 6.19. Found: C, 57.78; H, 9.66; N, 3.05; P, 6.28.

EXAMPLE 29

3,6-Dioxanonadecyl 2-trimethylammonioethyl phosphate 5 g (0.0173 mole) of 2-[2-(tridecyloxy)ethoxy]ethanol is dissolved in 40 ml of benzene, 6.7 g (0.0277 mole) of 2-bromoethyl phosphorodichloridate and 2.2 g (0.0277 mole) of pyridine are added, and the mixture is stirred at room temperature. The reaction mixture is concentrated under reduced pressure, and the residue is subjected to hydrolysis by adding water thereto, made acidic with hydrochloric acid and extracted with ether. The ether extract is concentrated to dryness, dissolved in a solution of trimethylamine in toluene, and allowed to react with the amine at 60° C. Purification of the product by the procedure of Example 7 gives 1.4 g (18% yield) of a colorless powder.

IR (KBr) cm$^{-1}$: 3420, 2920, 2852, 1460, 1230, 1084, 960, 788.

TLC [silica gel, CHCl$_3$:MeOH:H$_2$O (65:25:4)] R$_f$=0.15, one spot.

Elemental analysis: Calculated for $C_{22}H_{48}NO_6P$: C, 58.25; H, 10.67; N, 3.09; P, 6.83. Found: C, 58.24; H, 11.04; N, 3.38; P, 6.76.

EXAMPLE 30

3,6-Dioxaoctadecyl 2-thiazolioethyl phosphate 3,6-Dioxaoctadecyl 2-bromoethyl phosphate (2.5 g) and thiazole (5.0 g) are mixed and heated at 60° C. The excess thiazole is removed under reduced pressure, silver carbonate and methanol are added to the residue, and the mixture is heated under reflux. The insolubles are filtered off, the filtrate is concentrated to dryness, and the residue is purified twice by silica gel column chromatography (developing solvent: methanol; chloroform-methanol-water). There is obtained 0.78 g of the title compound.

IR (KBr) cm$^{-1}$: 3350, 2920, 2850, 1660, 1460, 1230, 1058, 750.

TLC [silica gel, CHCl$_3$:MeOH:H$_2$O (65:25:4)]:R$_f$=0.25, one spot.

Elemental analysis: Calculated for $C_{21}H_{40}NO_6PS \cdot \frac{1}{2}H_2O$: C, 53.14; H, 8.70; N, 2.95; P, 6.53; S, 6.76. Found: C, 52.88; H, 8.97; N, 3.23; P, 6.80; S, 7.02.

NMR (60 MHz, CHCl₃) δ: 0.90(3H), 1.3(20H), 3.3–5.3(14H), 8.48, 8.80 and 10.96(1H and thiazolium, respectively).

EXAMPLE 31

3,6-Dioxaoctadecyl 2-(4-carbamoylpyridinio)ethyl phosphate 3,6-Dioxaocetadecyl 2-bromoethyl phosphate (3 g) and isonicotinic acid amide (3 g) are dissolved in toluene (60 ml), and the solution is heated at 110° C. The solvent is then distilled off, silver carbonate and methanol are added, and the mixture is heated under reflux. The insolubles are filtered off, the filtrate is concentrated to dryness, and the residue is purified twice by silica gel chromatography (developing solvent: methanol; chloroform-methanol-water). There is obtained 0.9 g of the title compound.

IR (film) cm⁻¹: 3375, 2920, 2850, 1685, 1640, 1565, 1460, 1230, 1098, 1045, 920, 775.

Elemental analysis: Calculated for $C_{24}H_{43}N_2O_7P\cdot\frac{1}{2}H_2O$: C, 56.34; H, 8.67; N, 5.48; P, 6.05. Found: C, 56.57; H, 8.69; N, 5.58; P, 6.15.

NMR (60 MHz, D₂O) δ: 0.8(3H), 1.3(20H), 3.4–5.5(14H), 8.56(2H, d, J=7 Hz), 9.30(2H, d, J=7 Hz).

EXAMPLE 32

3,6-Dioxaoctadecyl 2-isoquinolinioethyl phosphate 3,6-Dioxaoctadecyl 2-bromoethyl phosphate (3.0 g) and isoquinoline (3 g) are dissolved in toluene (30 ml) and warmed at 60° C. The solvent is distilled off, silver carbonate and methanol are added to the residue, and the mixture is refluxed. The insolubles are filtered off, the filtrate is concentrated to dryness, and the residue is purified twice by silica gel chromatography (developing solvent: methanol; chloroform-methanol-water). There is obtained 0.5 g of the title compound.

IR(film) cm⁻¹: 3350, 2920, 2850, 1640, 1460, 1398, 1242, 1053, 745.

Elemental analysis: Calculated for $C_{27}H_{44}NO_6P$: C, 63.63; H, 8.70; N, 2.75; P, 6.08. Found: C, 63.27; H, 8.95; N, 2.89; P, 5.87.

NMR (60 MHz, CDCl₃) δ: 0.88(3H), 1.3(20H), 3.3–5.6(14H), 7.5–9.5(6H, m, quinolinium), 10.8(1H, s, quinolinium).

EXAMPLE 33

3,6-Dioxaoctadecyl 2-pyridazinioethyl phosphate 3,6-Dioxaoctadecyl 2-bromoethyl phosphate (3.0 g) and pyridazine (5 g) are dissolved in toluene (60 ml) and warmed at 60° C. The solvent is distilled off, silver carbonate and methanol are added, and the mixture is refluxed. The insolubles are filtered off, the filtrate is concentrated to dryness, and the residue is purified by silica gel chromatography (developing solvent: chloroform-methanol-water) to give 1.2 g of the title compound.

TLC [silica gel, CHCl₃:MeOH:H₂O (65:25:4)]: $R_f$=0.2

IR (film) cm⁻¹: 3350, 2910, 2850, 1645, 1582, 1460, 1230, 1060, 940, 780.

NMR (60 MHz, CDCl₃) δ: 0.88(3H), 1.3(20H), 3.2–5.4(14H), 8.88(2H), 9.60(1H), 10.23(1H).

Elemental analysis: Calculated for $C_{22}H_{52}N_2O_6P\cdot 0.5H_2O$: C, 56.07; H, 10.84; N, 5.69. Found: C, 56.30; H, 10.66; N, 5.88.

EXAMPLE 34

3,6-Dioxaeicosyl 2-pyridinioethyl phosphate

2-[2-(Tetradecyloxy)ethoxy]ethyl 2-bromoethyl phosphate obtained in Example 26 is reacted with pyridine and a conventional purification procedure of the reaction mixture gives the title compound as colorless solid.

TLC: $R_f$=0.15, one spot [CHCl₃:MeOH:H₂O (65:25:4)]

IR (KBr) cm⁻¹: 3410, 2925, 2855, 1634, 1492, 1465, 1240, 1075, 934.

Elemental analysis: Calculated for $C_{25}H_{46}NO_6P\cdot H_2O$: C, 59.39; H, 9.57; N, 2.77; P, 6.12. Found: C, 59.48; H, 9.62; N, 2.88; P, 6.24.

EXAMPLE 35

3,6-Dioxaheneicosyl 2-pyridinioethyl phosphate

In the same manner as above, 2-[2-(pentadecyloxy)ethoxy]ethyl 2-bromoethyl phosphate is reacted with pyridine to give the title compound.

TLC: $R_f$=0.15, one spot [CHCl₃:MeOH:H₂O (65:25:4)].

IR (KBr) cm⁻¹: 3410, 2920, 2850, 1630, 1490, 1240, 1074.

Elemental analysis: Calculated for $C_{26}H_{48}NO_6P\cdot H_2O$: C, 60.09; H, 9.70; N, 2.70; P, 5.96. Found: C, 60.07; H, 9.93; N, 2.67; P, 6.36.

TEST 1

The cell proliferation inhibiting activity (GD₅₀ value) of the compound obtained in Example 7 is 8–11 µg/ml against mouse spontaneous myelocytic leukemia cells MI (resistant clone) and 2–3 µg/ml against Rauscher virus-induced promyelocytic leukemia cells R453. The growth inhibiting effect (IG effect) and differentiation induing activity of several compounds in accordance with this invention against human myelocytic leukemia cells HL-60 are as shown in Table 1. The experiment was carried out by the method of R. Gallo et al. described in Blood, Vol 54, No. 3, 713 (1979).

TABLE 1

| Test compound (Example No.) | Effect on human myelocytic leukemia cells | |
|---|---|---|
| | IG effect on HL-60 $GD_{50}$ (µg/ml)* | Differentiation inducing activity against HL-60 |
| 5 | 1–2 | + |
| 7 | 1–2 | ++ |
| 10 | 1–2 | + |
| 11 | 5 | + |
| 12 | 5 | + |
| 13 | 1–2 | + |
| 14 | 2 | + |
| 15 | 3.6 | ++ |
| 19 | 3.2 | ++ |
| 24 | 2.8 | ++ |
| 25 | 3.6 | + |
| 26 | 1.5 | ++ |
| 28 | 2.9 | ++ |
| 31 | 6.0 | + |

*5 day culture

TEST 2

The antiprotozoal and antimycotic (antifungal) activities of some compounds in accordance with this invention are as shown in Table 2 and Table 3.

Referring to the antiprotozoal activity given in Table 2, the microbial growth inhibiting activity (MIC) of each compound of this invention was assayed by the broth dilution method by incubating *Tetrahymena pyriformis* W strain as the test organism at 28° C. for 44–48 hours, using a test culture medium comprising 20 g of Tryptose peptine (Difco), 1 g of yeast extract, 2 g of glucose, 1,000 ml of distilled water and 10 ml of 1M phosphate buffer (pH 7.0).

Referring to the antimycotic activity presented in Table 2, *Cryptoccocus neoformans* and others were used as the test microbes, a paper disk (8 mm in diameter) was immersed in an aqueous solution of each test compound having a concentration of 3 mg/ml, air dried and placed on an agar medium, then incubation was conducted at 37° C. for 2 days, and the inhibition circle was measured. When the diameter of the inhibition circle was not larger than 8 mm, 8–10 mm, 10–20 mm, or larger than 20 mm, the activity was judged as −, ±, + or ++, respectively.

Referring to the antifungal activity shown in Table 3, a variety of typical phytopathogenic fungi were used as the test organisms, and the minimum inhibitory concentration (MIC) values were determined by the serial dilution method using 1% glucose-bouillon agar medium.

TABLE 2

| Antiprotozoal and antimycotic activities | | | | |
|---|---|---|---|---|
| Test compound (Example No.) | MIC (µg/ml) Tetrahymena | Growth inhibition | | |
| | | Crypto-coccus | Rhodo-torula | Hamigera |
| 7 | 0.4 | ++ | + | ++ |
| 12 | 2–4 | ++ | + | + |
| 13 | 4 | + | + | + |
| 14 | 4 | + | + | + |
| 15 | >4 | ++ | + | + |
| 16 | >4 | ++ | + | + |
| 2 | >4 | ± | + | − |
| 8 | >4 | ... | ... | ... |
| 3 | >4 | − | ... | ... |
| 5 | 4 | ± | ... | ... |
| 10 | >4 | + | ... | ... |
| 24 | 1–2 | + | ... | ... |
| 18 | ≧4 | + | ... | ... |
| 25 | 0.4 | ++ | ... | ... |
| 21 | 2 | + | ... | ... |
| 22 | 4 | − | ... | ... |
| 26 | 0.2 | + | ... | ... |
| 28 | 4 | ++ | ... | ... |
| 32 | 4 | ++ | ... | ... |
| 29 | ≦1 | ++ | ... | ... |
| 34 | 4 | + | ... | ... |

TABLE 3

| Antifungal activity of the compound of this invention | | | | | | | | | | | |
|---|---|---|---|---|---|---|---|---|---|---|---|
| | MIC (µg/ml) Test compound (Example No.) | | | | | | | | | | |
| Test phytopathogenic fungus | Ex. 7 | Ex. 12 | Ex. 13 | Ex. 15 | Ex. 16 | Ex. 24 | Ex. 18 | Ex. 25 | Ex. 26 | Ex. 29 | Ex. 28 |
| (1) *Pyricularia oryzae* (rice blast) | 3.12 | 100 | 100 | 25 | 25 | 25 | 12.5 | 12.5 | 3.12 | 6.25 | 6.25 |
| (2) *Cochliobolus miyabeanus* (rice Helminthosporium leaf spot) | 25 | 50 | 50 | 25 | 25 | 100 | >100 | 25 | 12.5 | 25 | 25 |
| (3) *Botrytis cinerea* (gray mold) | 6.25 | 50 | 50 | 12.5 | 12.5 | 25 | 25 | 6.25 | 6.25 | 25 | 12.5 |
| (4) *Leptosphaeria salvinii* (rice stem rot) | 25 | — | — | 25 | 25 | >100 | 12.5 | 6.25 | 6.25 | 12.5 | 12.5 |
| (5) *Sclerotinia sclerotiorum* (kidney bean stem rot) | — | 25 | 25 | 25 | 50 | 50 | >100 | 25 | 50 | 100 | 25 |
| (6) *Colletotrichum lagenarium* (cucumber anthracnose) | 25 | 25 | 25 | 12.5 | 12.5 | 25 | >100 | 1.56 | 1.56 | 3.12 | 6.25 |
| (7) *Aspergillus niger* (black mold) | 25 | 25 | 25 | 25 | 25 | 12.5 | >100 | 25 | 12.5 | 25 | 25 |
| (8) *Penicillium niger* (blue mold) | — | — | — | 12.5 | 12.5 | 6.25 | >100 | 12.5 | 12.5 | 12.5 | 12.5 |
| (9) *Saccharomyces cerevisiae* (brewer's yeast) | 12.5 | 100 | 100 | 50 | 50 | — | — | 12.5 | 6.25 | 12.5 | — |

DOSAGE FORM EXAMPLE 1

3,6-Dioxaeicosyl 2-trimethylammonioethyl phosphate (80 g) is dissolved in 1 liter of distilled water, the solution is passed through a sterilization filter, poured into 1,000 vials (1 ml per vial) and lyophilized, and the vials are tightly stoppered.

Separately, a solution containing xylitol or mannitol (100 g in 2 liters) in distilled water for injection is poured into 1,000 ampules for injectable solution (2 ml per ampule) in an aseptic manner, and the ampules are sealed by fusing.

For administration, the powder in one vial is dissolved in the above-mentioned xylitol (or mannitol) solution in one ampule.

DOSAGE FORM EXAMPLE 2

Tablets, each weighing 370 mg and having a diameter of 9.5 mm, are prepared in a conventional manner by mixing the ingredients:
  (1) 3,6-Dioxatetracos-15(Z)-enyl 2-trimethylammonioethyl phosphate: 100 mg per tablet
  (2) Lactose: 200 mg per tablet
  (3) Corn starch: 51 mg per tablet
  (4) Hydroxypropylcellulose: 9 mg per tablet
followed by granulation, addition of corn starch (8 mg per tablet) and magnesium stearate (2 mg per tablet) and tableting.

DOSAGE FORM EXAMPLE 3

Tablets containing 2-[2-(dodecyloxy)ethoxy]ethyl 2-pyridinioethyl phosphate are prepared in the same manner as in Dosage Form Example 2, and coated with a solution of hydroxypropylmethylcellulose phthalate (14 mg per tablet) and castor oil (1 mg per tablet) in an acetone-ethanol (4:6) mixture, the concentration of the solutes being 7%. Thus are obtained enteric coated tablets.

What is claimed is:

1. A compound of the formula:

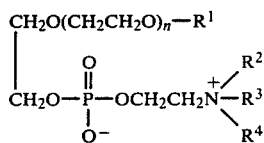

wherein n is an integer of 1 to 15;

$R^1$ is $C_{6-26}$ alkyl, $C_{6-26}$ alkenyl or $C_{6-26}$ alkynyl, each of said groups being unsubstituted or substituted by hydroxyl, mercapto, amino, oxo, carbamoyl, carboxyl, halogen, $C_{3-7}$ cycloalkyl or phenyl; and $R^2$, $R^3$ and $R^4$ are independently hydrogen or $C_{1-5}$ alkyl, or

represents cyclic ammonio selected from the group consisting of pyridinio, oxazolio, thiazolio, pyridazinio, quinolinio, isoquinolinio, N-$C_{1-4}$ alkylmorpholinio and N-$C_{1-4}$ alkylpiperazinio, each of said groups being unsubstituted or substituted by $C_{1-4}$ alkyl, hydroxyl, hydroxyethyl, aminoethyl, amino, carbamoyl or ureido, or a pharmaceutically acceptable salt thereof.

2. A compound according to claim 1, wherein n is an integer of 1 to 9.

3. A compound according to claim 2, wherein n is an integer of 1 to 4.

4. A compound according to claim 1, wherein $R^1$ is $C_{10-20}$ alkyl or $C_{10-20}$ alkenyl.

5. A compound according to claim 1, wherein $R^2$, $R^3$ and $R^4$ are hydrogen or methyl.

6. A compound according to claim 1, wherein the cyclic ammonio is pyridinio, thiazolio, pyridazinio or isoquinolinio, said group being unsubstituted or substituted by carbamoyl.

7. The compound according to claim 1, which is 3,6-dioxatetracos-15(Z)-enyl 2-trimethylammonioethyl phosphate.

8. The compound according to claim 1, which is 2-[2-(dodecyloxy)ethoxy]ethyl 2-pyridinioethyl phosphate.

9. The compound according to claim 1, which is 3,6-dioxaeicosyl 2-trimethylammonioethyl phosphate.

10. The compound according to claim 1, which is 3,6-dioxanonadecyl 2-pyridinioethyl phosphate.

11. The compound according to calim 1, which is 3,6-dioxaeicosyl 2-pyridinioethyl phosphate.

12. The compound according to claim 1, which is 3,6-dioxaoctadecyl 2-thiazolioethyl phosphate.

* * * * *